United States Patent [19]

Hsieh

[11] Patent Number: 4,823,017

[45] Date of Patent: Apr. 18, 1989

[54] SCINTILLATION CAMERA AND MULTIFOCAL FAN-BEAM COLLIMATOR USED THEREIN

[75] Inventor: Jiang Hsieh, Elk Grove Village, Ill.

[73] Assignee: Siemens Gammasonics, Inc., Des Plaines, Ill.

[21] Appl. No.: 944,700

[22] Filed: Dec. 19, 1986

[51] Int. Cl.$^4$ .................. G01T 1/164; G21K 1/02
[52] U.S. Cl. .................. 250/363.03; 250/505.1
[58] Field of Search .................. 250/363 SH, 505.1; 378/149

[56] References Cited

U.S. PATENT DOCUMENTS

| 3,688,113 | 8/1972 | Miraldi | 250/363 SB |
| 3,777,148 | 12/1973 | Miraldi | 378/149 |
| 4,250,392 | 2/1981 | Leask et al. | 250/505.1 |
| 4,670,657 | 6/1987 | Hawman et al. | 250/505.1 |

FOREIGN PATENT DOCUMENTS

| 2351450 | 4/1975 | Fed. Rep. of Germany. | |
| 1561351 | 2/1969 | France. | |
| 223081 | 12/1983 | Japan | 250/363 SH |

Primary Examiner—Carolyn E. Fields
Attorney, Agent, or Firm—Mark H. Jay

[57] ABSTRACT

A fan-beam collimator has a plurality of focal lengths. The shortest focal length is located at the center of the collimator. The longest focal length is located at the periphery of the collimator. The focal length increases between the minimum focal length and the maximum focal length.

7 Claims, 4 Drawing Sheets

SCINTILLATION CAMERA AND MULTIFOCAL FAN-BEAM COLLIMATOR USED THEREIN

BACKGROUND OF THE INVENTION

The invention relates to scintillation cameras, and more particularly relates to scintillation cameras for transaxial ECT (Emission Computed Tomography) imaging. In its most immediate sense the invention relates to tomographic imaging of relatively small body organs such as the heart.

When constructing tomographic images of a small body organ (such as the heart) using transaxial ECT, the scintillation camera head with a collimator attached is rotated around the patient. To prevent the tomographic image from being marred by artifacts, it is necessary to image not merely the heart alone, but the entire slice of the body in which the heart is located. When the collimator used is a fan-beam collimator, the collimator conventionally has a comparatively long focal length, such as 130 centimeters, so that the views of the body are not truncated. This in turn insures that there is complete sampling around the heart and prevents artifacts caused by truncation.

This focal length is appropriate for imaging the periphery of the body, but it inappropriately establishes the sensitivity of the collimator. This is because for fixed resolution and radius of rotation, sensitivity decreases as focal length increases. By choosing a single focal length which is just long enough to include the periphery of the body, the sensitivity gain of the collimator is limited by the periphery of the body (which is not generally of interest) rather than by a central body organ of interest (i.e. the heart).

It is therefore one object of the invention to provide a transaxial ECT scintillation camera system which has improved sensitivity in its center without causing truncation errors and corresponding artifacts.

It is another object to provide such a system which will improve images of comparatively small body organs, such as the heart.

It is another object to, in general, improve on known systems of this type.

SUMMARY OF THE INVENTION

In accordance with the invention, there is provided a scintillation camera system which uses a fan-beam collimator which has a plurality of focal lengths. Advantageously, the collimator focuses to a plurality of focal points which are advantageously colinear and advantageously aligned with a centerline of the collimator. Advantageously, the focal length of the collimator is at a minimum value adjacent a centerline of the collimator and is at a maximum value adjacent peripheral regions of the collimator. Further advantageously, the focal length of the collimator changes (either continuously or stepwise) from the minimum value to the maximum value, and does not decrease with increasing distance from the centerline.

Because the focal length of the collimator is at a minimum in the center of the collimator, there is a large gain in sensitivity in the center of the collimator. Because the focal length at the peripheral regions of the collimator is long enough, the reconstruction artifacts caused by truncation can be avoided.

The invention therefore provides an overall gain in sensitivity in the center of the collimator without any corresponding truncation error at the periphery of the collimator. This permits a better image to be produced in the same period of time, or alternatively permits an equally good image to be produced faster.

BRIEF DESCRIPTION OF THE DRAWINGS

Exemplary and non-limiting preferred embodiments of the invention are shown in the drawings, in which.

DETAILED DESCRIPTION OF PREFERRED EMBODIMENTS

Figure 2:
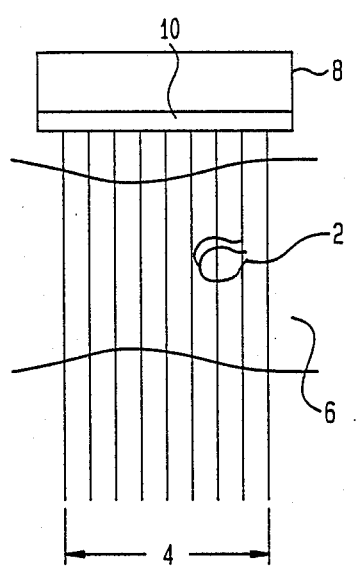
FIG. 2 is a schematic axial view of the first preferred embodiment.

In the following description, it will be assumed that the inventionn will be used to image a patient's heart. However, it will be understood that this need not be the case and that any other organ can be imaged instead.

To image a patient's heart 2 it is necessary to image a slice 4 of the chest of a patient who is generally indicated by reference numeral 6. This slice 4 is approximately 17 cm in radius. To image this slice 4, a conventional scintillation camera head 8 and attached collimator 10 are rotated along a scan path 12 which is 20 cm in radius.

At the center of the collimator 10, along a centerline 10C thereof, the collimator 10 has a fan-beam configuration with a focal length 3 of 45 cm, i.e. long enough to place the focal point 14 just outside the patient 6. At the peripheral regions 16 of the collimator 10, the focal length 18 is at its maximum, here 130 cm. This focal length 18 is long enough so there is no truncation of any part of the slice 4 because the view of the collimator 10 is slightly wider than the width of the patient 6.

In the first preferred embodiment, the collimator 10 has a focal length which varies continuously with distance; advantageously, the focal length f is determined by the equation:

$$f = R + \frac{R}{\left(\frac{f_{min}}{f_{min} - R}\right)\left(\frac{w - x}{w}\right)^2 + \left(\frac{f_{max}}{f_{max} - R}\right)\left(\frac{x}{w}\right)^2}$$

$w$ = half width of collimator $x$ = distance from center where $R$ = radius of rotation;

$f_{min}$ = minimum value of $f$;

$f_{max}$ = maximum value of $f$

Figure 1:
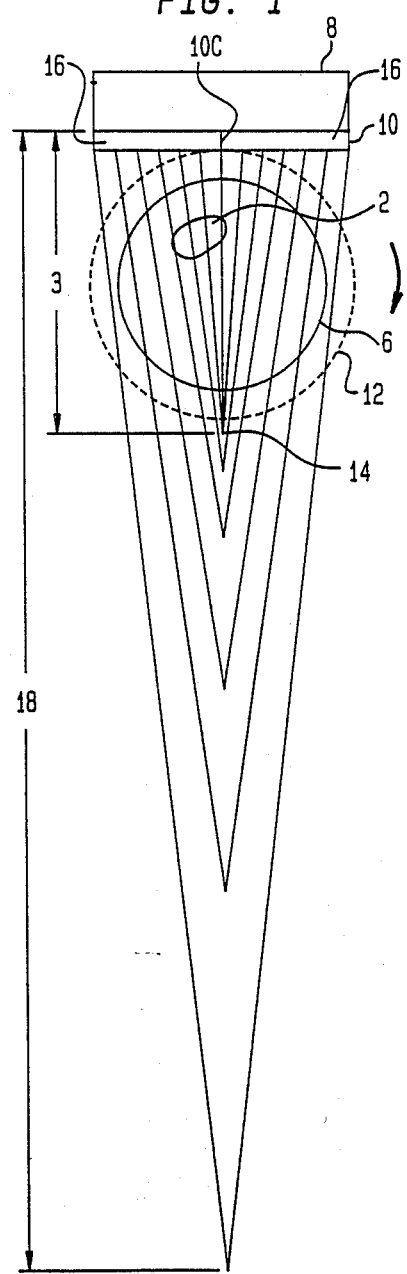
FIG. 1 is a schematic transaxial view of a first preferred embodiment of the invention.

It will be understood that FIGS. 1 and 2 are exaggerated for clarity and that there will be hundreds of closely spaced focal points rather than the six which are shown spaced widely apart.

Figure 3:
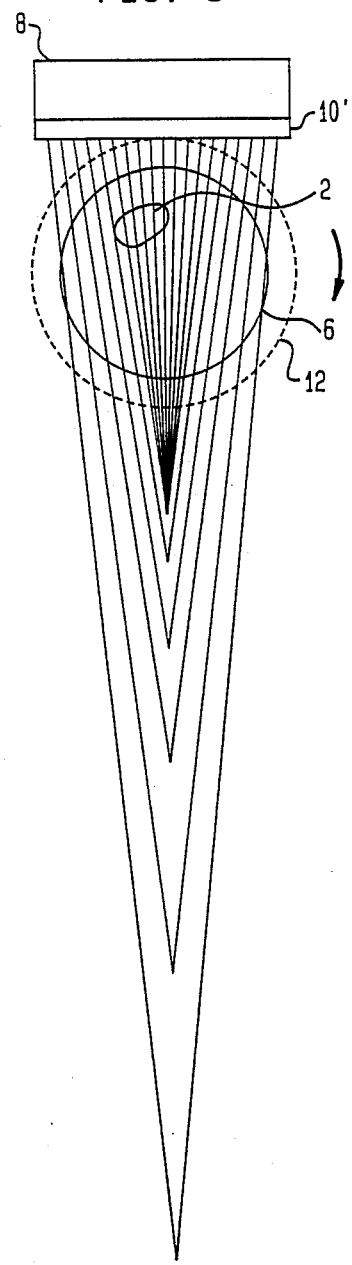
FIG. 3 is a schematic transaxial view of a second preferred embodiment.

Alternatively, the focal length may vary discontinuously, e.g. the focal length may be substantially constant over a central region of collimator 10 and vary over the peripheral regions; this is illustrated in FIG. 3. FIG. 3 is illustrative; there will be more than six focal points, but FIG. 3 has been exaggerated for clarity.

With the focal lengths chosen, the sensitivity of the 10 and 10' collimators at the center are 1.8 times the sensitivity of a parallel-hole collimator of equivalent resolution.

Because the focal length of the collimator varies, the magnification of the image varies as a function of position. To take this into account, the geometrical relationships illustrated in FIG. 4 may be utilized.

Figure 4:
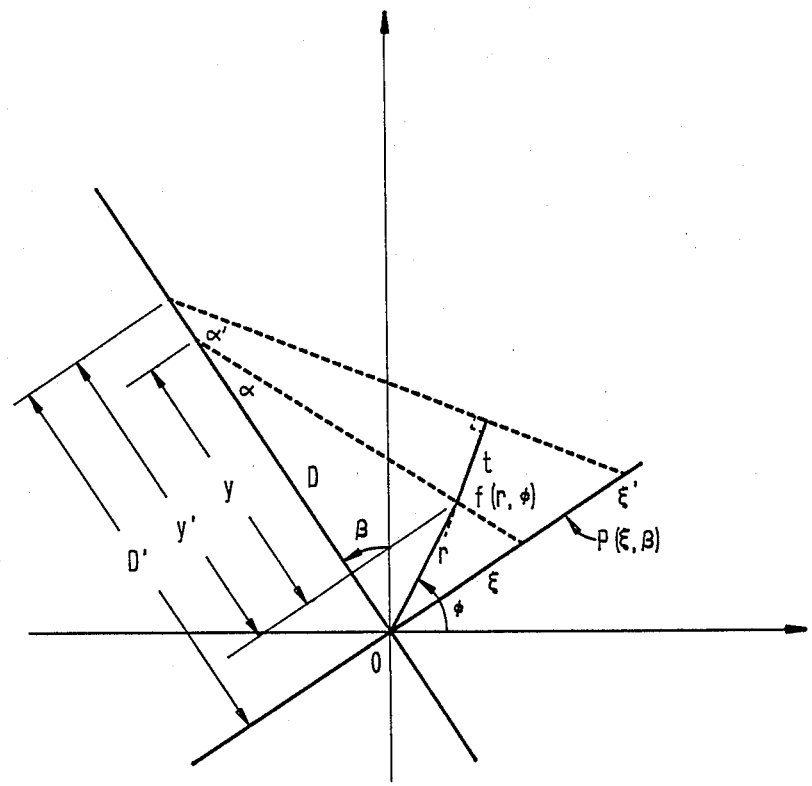
FIG. 4 is a diagram illustrating the geometry of the preferred embodiment.

In FIG. 4, $f(r, \phi)$ represents the point to be reconstructed and $P(\xi,\beta)$ represents the projection image acquired during a single view. A representation of $f(r,\phi)$ is given by $$f(r,\phi) = \frac{1}{4\pi 2} \int_0^{2N} g''(d,\beta) \frac{D^2}{[D + \gamma\sin(\beta - \phi)]^2} d\beta$$

where $g''(\xi,\beta)$ is the filtered and normalized image acquired during the view under construction and is given by $$g''(d,\beta) = \int_{-\infty}^{\infty} \left(\frac{\rho^2 + D'^2}{D'^2}\right) F_e\left[\rho - \frac{6}{6'}\rho'\right] J \cdot P(\rho^1,\beta) d\rho$$

where $$J = \frac{\partial D'}{\partial \rho'} \sin\alpha' + \frac{\partial \alpha'}{\partial \rho'} D'\cos\alpha; \; 6 = \frac{D}{Y} \; 6' = \frac{D'}{Y'}$$

and $F_E$ is the convolution filter.

Figure 5:
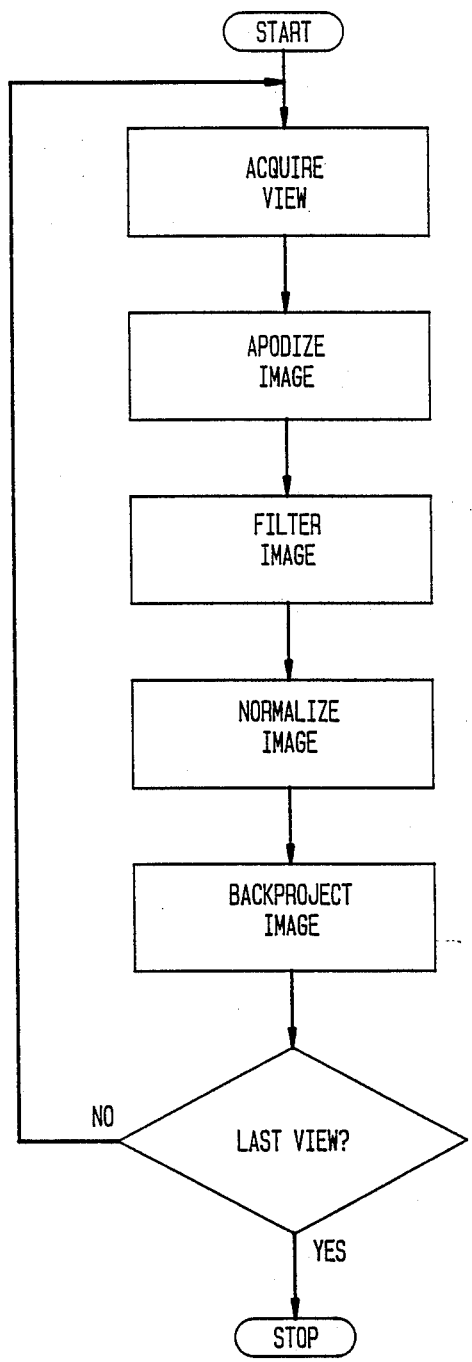
FIG. 5 is a flowchart of a preferred method of using the invention.

If it is assumed that the convolution filter is spatially invarient, computation speed can be increased, and the image reconstruction process can follow the flow chart shown in FIG. 5.

First, the individual view is acquired. Next, the image is apodized, because apodization is a necessary step whenever a fan beam collimator is used to produce a tomographic image. Next, the apodized image is filtered (deconvoluted), and the apodized and filtered view if normalized to correct for the different magnifications caused by the different focal lengths of the collimator. The apodized, filtered and normalized image is then backprojected into the image space and added to whatever previously processed data is present there. This process is repeated for each view until all views have been acquired.

Those skilled in the art will understand that changes can be made in the preferred embodiments here described, and that these embodiments can be used for other purposes. Such changes and uses are within the scope of the invention, which is limited only by the claims which follow.

What is claimed is:

1. A scintillation camera system, comprising a scintillation camera head and fan-beam collimator having a plurality of focal lengths.

2. A scintilation camera system, comprising a scintillation camera head and a fan-beam collimator which focuses to a plurality of coplanar focal points.

3. The scintillation camera system of claim 2, wherein the focal points are all coplanar with a centerline of the collimator.

4. A fan-beam collimator having a plurality of focal lengths, the focal length of the collimator being at a minimum value adjacent a centerline of the collimator, the focal length of the collimator being at a maximum value adjacent two opposed peripheral regions thereof and the focal length of the collimator nondecreasing from said minimum value to said maximum value as distance from said centerline increases.

5. The collimator of claim 4, wherein the focal length of the collimator varies in discrete steps.

6. The collimator of claim 4, wherein said minimum value is approximately 45 cm and said maximum value is approximately 130 cm.

7. The collimator of claim 4, wherein the focal length of the collimator varies in such small discrete steps as to simulate continuous variation.

* * * * *